United States Patent [19]

Heyde

[11] Patent Number: 4,961,923

[45] Date of Patent: Oct. 9, 1990

[54] IRRIGANTS FOR USE IN SCALING AND/OR LAVAGE APPARATUS

[75] Inventor: John B. Heyde, Milford, Del.

[73] Assignee: Dentsply Management Corp., York, Pa.

[21] Appl. No.: 418,780

[22] Filed: Oct. 2, 1989

Related U.S. Application Data

[63] Continuation of Ser. No. 157,672, Feb. 19, 1988, abandoned.

[51] Int. Cl.$^5$ .................... A61K 7/16; A61K 7/24; A61C 1/07
[52] U.S. Cl. .................... 424/49; 424/55; 424/54; 433/86
[58] Field of Search .................... 424/49, 55; 433/86

[56] References Cited

U.S. PATENT DOCUMENTS

| | | | |
|---|---|---|---|
| 3,864,472 | 2/1975 | Pensak et al. | 424/54 |
| 3,887,701 | 6/1975 | Nachitigal | 424/54 |
| 3,947,570 | 3/1976 | Pensak et al. | 424/54 |
| 4,022,880 | 5/1977 | Vinson et al. | 424/49 |
| 4,150,151 | 4/1979 | Pader et al. | 424/49 |
| 4,160,821 | 6/1979 | Sipos | 424/49 |
| 4,289,755 | 9/1981 | Dhabhar | 424/55 |
| 4,315,742 | 2/1982 | Nash et al. | 433/86 |
| 4,325,939 | 4/1982 | Shah | 424/55 |
| 4,339,432 | 7/1982 | Ritchey et al. | 424/54 |
| 4,374,122 | 2/1983 | Stroz et al. | 424/48 |
| 4,425,325 | 1/1984 | Ritchey et al. | 424/54 |
| 4,435,380 | 3/1984 | Pader | 424/49 |
| 4,465,661 | 8/1984 | Schmolka | 424/58 |
| 4,472,373 | 9/1984 | Ryan | 424/54 |
| 4,483,848 | 11/1984 | Cox et al. | 424/49 |
| 4,508,713 | 4/1985 | Stroz et al. | 514/60 |
| 4,522,806 | 6/1985 | Muhlemann et al. | 424/52 |
| 4,582,702 | 4/1986 | Grollier | 424/52 |
| 4,601,900 | 7/1986 | Noponen et al. | 424/54 |
| 4,632,937 | 12/1986 | Lynch | 514/470 |
| 4,770,634 | 9/1988 | Pellico | 433/217.1 |
| 4,800,095 | 1/1989 | Carroll et al. | 426/548 |

FOREIGN PATENT DOCUMENTS

| | | |
|---|---|---|
| 961412 | 1/1975 | Canada . |
| 988431 | 5/1976 | Canada . |
| 1001554 | 12/1976 | Canada . |
| 1028623 | 3/1978 | Canada . |
| 1034505 | 7/1978 | Canada . |
| 1042806 | 11/1978 | Canada . |
| 1087098 | 10/1980 | Canada . |
| 1095422 | 2/1981 | Canada . |
| 1104939 | 7/1981 | Canada . |
| 1116091 | 1/1982 | Canada . |
| 1122123 | 4/1982 | Canada . |
| 1139229 | 1/1983 | Canada . |
| 1161860 | 2/1984 | Canada . |
| 1168159 | 5/1984 | Canada . |
| DE3023461 | 1/1981 | Fed. Rep. of Germany . |
| DE3001575 | 7/1981 | Fed. Rep. of Germany . |
| 1469399 | 4/1977 | United Kingdom .................. 433/86 |

*Primary Examiner*—A. Lionel Clingman
*Attorney, Agent, or Firm*—Edward J. Hanson, Jr.

[57] ABSTRACT

Irrigants to be used with vibratory scaling apparatus and lavage are provided. The irrigants of the invention are characterized in that they contain medicaments for the treatment of conditions in the mouth and have a viscosity and deliquescence adapted to substantially optimize the efficiency of the apparatus. The irrigants are formulated so that they have minimal stickiness on drying, minimal foaming and do not gum-up the apparatus in which they are used. Also provided is a method for treating dental diseases comprising applying the irrigants of the invention through a vibratory scaling apparatus to substantially optimize the efficiency of said apparatus and to substantially optimize destruction and removal of infectious bacteria using said apparatus and the removal or inactivation of endotoxins derived from bacteria or the host.

14 Claims, No Drawings

IRRIGANTS FOR USE IN SCALING AND/OR LAVAGE APPARATUS

This is a continuation of application Ser. No. 157,672, filed Feb. 19, 1988, now abandoned.

BACKGROUND OF THE INVENTION

The present invention relates to irrigants for use in apparatus used for scaling of teeth and for lavage of the gingival sulcus and cleaning the sulcular crevice.

The present invention especially relates to irrigants for use in apparatus for high velocity mechanical dental scaling with simultaneous lavage to debride teeth and clear the gingival sulcus.

It is known in the art that plaque and calculus harbor toxic and irritating components implicated in oral disease and that plaque and calculus can be removed from teeth by mechanical scaling, especially at high frequency, and especially at ultrasonic frequencies.

It is also known that the delivery of antimicrobial solutions in the form of lavage has potential therapeutic effect by delivery of medicaments directly to an affected site. Prior art devices comprise thin needle-like delivery tips through which medicaments of various sort may be delivered to the periodontal pocket. There is no vibratory or scaling potential with these devices. Rather any benefit results exclusive from the in-situ delivery of the medicament to the affected pocket.

By contrast, in copending application, U.S. Ser. No. 141,355 assigned to Dentsply International ®, incorporated herein by reference, disclosure was made of a fine but mechanically substantial device for delivery of medicaments to an affected site that is simultaneously activated to vibrate and to mechanically debride a periodontal pocket of calculus, bacteria and cellular debris. In the device described, the irrigant issues from the tip of the scaler, and one or more irrigants may be delivered simultaneously. Advantages for such a device are that irrigants may be delivered at the deepest location in a pocket so that when the calculus and plaque are debrided by the action of the scaler, debris may be removed from an affected periodontal pocket, for example, to the mouth. The irrigant is then evacuated by suction to remove debrided material.

In prior art lavage devices the irrigants chosen are those widely available as mouthwashes. These comprise a medicament and a vehicle. Medicaments of implied value include, for example, sanguinarine, chlorhexedine, cetylpyridinium chloride and the like. The vehicle most frequently comprises water, surfactants, a humectant and flavor enhancer typified by glycerin or sorbitol, a viscosity control agent typified by polyoxamer, ethanol as a cosolvent for otherwise immiscible ingredients, flavoring and sweetening agents to disguise otherwise unpalatable taste, a dispersant or surfactant to enhance the miscibility of the ingredients, and coloring agents. The selection of the ingredients is based generally on flavor perception and stabilization of the solution Examples of commercially available mouthwashes include Listerine, Listermint, Scope, Lavoris, Plax, Chloraseptic, Cepacol The active medicinal ingredients in these mouthwashes include phenol and substituted phenols, thymol, menthol, eucolyptol, methyl salicylate, benzoic acid, eugenol, zinc chloride, cetyl pyridinium chloride and chlorhexedine. The vehicles in all cases include ethanol. The humectants are glycerin and the higher molecular weight stabilizer viscosity control agent, polyoxamer.

Baer, Periodontal Case Reports, Vol 7, No. 1, 1985, has reported that the use of an ultrasonically activated instrument delivering a 3% solution of hydrogen peroxide subgingivally through its tip was a means to "change the environment within a periodontal pocket from anerobic to aerobic" and that the device with "hydrogen peroxide appears to be a safe and potentially adjunctive therapy modality worthy of further clinical trials" Other investigators have suggested the undesirability of applying peroxide in this manner predicated on its cellular toxicity.

In distinction over Baer, the present invention does not contemplate changing the normal oxygen tension within the sulcular tissue. Rather, it provides for removal of contaminating bacteria, toxic debris and antigen products, or the reaction, in situ, of antigens to passivate or inactivate them.

It is known that calculus and cellular debris may harbor antigenic components that trigger a series of reactions within the host that lead to the destruction of soft and hard tissue support of teeth Periodontal diseases are a major worldwide health problem. Collectively they are the major cause of tooth loss over the age of 35 years. The primary etiologic factor is bacterial plaque with dental calculus being a significant modifying influence which complicates treatment. Removal of both plaque and calculus is a prerequisite for improvement and maintenance of periodontal health An objective of the invention is to make materials and methods for the efficacious removal of dental plaque and calculus It has been found that the combination of high velocity scaling, especially ultrasonic scaling, with local delivery of an irrigant is advantageous Irrigants are delivered at the deepest location in a pocket so that when the calculus and plaque are debrided by the mechanical action of the scaler, debris is removed, for example, from an affected periodontal pocket to the mouth by continuous flow of the irrigant to the operative site The irrigant is then evacuated by suction to remove debrided material An objective of this treatment is to provide antimicrobial solutions locally so that resident bacteria may be killed and flushed, together with other noxious materials, from the deepest areas of a periodontal pocket.

Because heat is generated by the vibration of stacks and scaling tips, most prior art scaling devices have a conduit that transports tap water to the handpiece and onto the scaling tip for cooling thereof In magnetostrictive devices, for example, the tap water is first used to circulate around the tranducer stack to cool the stack, and is then dispensed onto the scaling tip to cool the tip In piezoelectric devices the cooling water is directed to the scaling tip only.

It has been suggested in copending U.S. Ser. No. 141,355 that irrigants used to deliver medicaments to the site of the treatment can also be used for cooling the stack and/or tip of a scaling instrument.

Also, the delivery of irrigant to the treatment site has the benefit of reducing the local temperature rise. Whether used supragingivally or subgingivally the repetitive vibratory action of the scaler, frequently at ultrasonic speeds, causes localized heating which can produce damage, especially to soft tissues. To avoid these effects, in the prior art, cooling water has been applied to the tip of the scaler by an open stream of cooling tap water delivered near the connection of the tip to the handle with the effect that when used subgingivally the cooling water sometimes could not physically access the action site because of intervening soft tissue. It is an objective of the present invention to provide methods and materials for cooling soft tissue locally so as to avoid traumatic thermal injury.

The irrigants may contain a surfactant which facilitates the removal of calculus and plaque from the tooth by reducing the surface tension of the crevicular fluid normally present so as to permit dislodgment of calculus and plaque. Further, a calcium chelating compound may be present in an irrigant to assist in the dislodgement of calculus, and the solvation, dispersion, and/or emulsification of the endotoxin permitting it being flushed from the tooth and/or soft tissue The irrigants may also contain inhibitors to antigenic components or enzymes and the like which can inactivate their biologic effect on the host. Such compounds are especially valuable in reducing pathogenic effect.

A beneficial effect of the use of surfactants and medicaments is believed to be their ability to disrupt the cell walls of infecting microorganisms to render them non-vital and to reduce their numbers significantly so that recolonization with consequent pathogenic effect is delayed or made impossible. Thus an extended period of time for healing and the growth of non-pathogenic microflora is permitted Plaque, especially subgingival plaque, is frequently consolidated into a sticky conglomerate that is difficult to disperse and remove. It is known industrially that ultrasonication of surfaces expedites dispersion and removal of contaminates, especially and importantly by aqueous solutions when surfactants are present. It is an objective to apply that methodology in dentistry to disperse, solvate and inactivate bacteria and bacterial plaque from periodontal pockets, soft tissue and teeth.

Endotoxins produced by pathogenic bacteria and host cells are believed to induce an inflammatory response which itself is harmful to the integrity of the periodontal attachment of soft tissue to the tooth resulting in pathogenic loss of gingival attachment level and reduction of the underlying bony support. Endotoxins of periodontopathogenic bacteria have demonstrated toxicity against human fibroblasts. These antigenic lipopolysaccaharides are resident in the first few hundred microns of tooth, and are incorporated into the calcified debris which is known as calculus The solubilization of these relatively hydrophobic residues and their removal from contaminated surfaces, for example from plastic tubing, is known to be difficult. It is an objective to provide irrigants containing surfactants and/or chelating agents combined with high velocity scaling and agitation of the irrigant in situ in such a manner that endotoxin is solvated, dispersed and/or emulsified to enhance and facilitate its removal from the sulcus Another mode of inactivating endotoxin to provide components capable of reacting with the endotoxin to render it non-antigenic. It is an objective to provide irrigants capable of producing such inactivation through the addition, for example, of monoclonal or polyclonal antibodies or reactive peptides or enzyme inhibitors.

Because the treatment may be painful the inclusion of an anesthetic may be desirable.

Irrigating solutions and medicaments may contain a variety of active ingredients that are often unpleasant tasting. To make them more palatable for the consumer it is often the practice to add sweeteners, flavors, and stabilizers that enhance the duration of the preferred taste for an extended period of time. The materials used for this purpose are commonly sorbitol and glycerin and similar hydroscopic polyols. These humectant polyols have, been found undesirable for use in lavage equipment because if they are left to dry in the fine orifices of the scaler or narrow tubing and ports of the supply system they occlude those apertures and make subsequent operation of the equipment difficult or impossible without first flushing with water. Similarly, if the compounds are splashed on hands, operating area or equipment surface, the dried residue is sticky and occludes debris in addition to being aesthetically unpleasant Also, it has been found that for proper flow rate the viscosity of the fluid must be maintained at a level which permits the fluid to flow freely in and from the equipment.

Also, prior art fluids have a tendency to foam which, although advantageous for fighting bacteria, has a tendancy to block the view of the operator from the field of treatment.

It is an object of the invention to provide irrigant formulations containing medicaments, that have a selected viscosity to have a desirable flow rate from the apparatus, do not foam excessively so that the view of the operator is not obstructed, are relatively non-sticky, and are pleasant tasting

SUMMARY OF THE INVENTION

In its preferred form the irrigant comprises a medicament and a vehicle and specifically comprises medicament, water, and optionally viscosity control agents, ethanol, flavors, sweeteners and dye.

Medicaments are selected from a broad range of compounds that are capable, when properly formulated into an irrigant, of dissolving, suspending, or emulsifying bacteria and bacterial plaque components including calculus, endotoxin and other antigenic factors when used in the device The continuous flow of irrigant into the pocket facilitates their removal from the sulcus.

Their solubilization, dispersion and emulsification is enhanced by the coincident use of the ultrasonic vibration of the instrument scaling tip within the periodontal pocket.

Irrigants of the invention for use in dental scaling and lavage apparatus comprise water, medicament, and optionally antifoaming agents, surfactants, viscosity control agents, flavors, sweetener and flavor enhancers. In a preferred embodiment the sweetener comprises aspartame, saccharin, xylitol, etc, and a viscosity control agent and flavor enhancer selected from among hydrogenated starch hydrolysates, a preferred example of which is Hystar 5875, ingredients which do not leave a sticky residue to clog the apparatus when used in the formulations of this invention. Medicaments are selected from a group of known medicaments for treating caries and periodontal disease; neutralizing antigenically active residues; inhibiting enzymes; solvating, suspending, dispersing or emulsifying endotoxin, plaque debris, and calculus; calcium chelators; anesthetics; astringents; antibiotics and anti-inflammatory compounds In its preferred form the irrigant comprises water, medicament, hydrogenated starch hydrolysate, surfactant, flavoring, sweeteners, and optionally ethanol for solvation of ingredients and dyes for coloring the compounds.

A method for treating periodontal diseases is provided which comprises simultaneous ultrasonic scaling and continuous delivery in situ of irrigating solutions to enhance removal and reduce counts of viable bacteria, bacterial debris, including calculus, endotoxin and other antigenic factors Topical anesthesia and the coincident delivery of astringent and anti-inflammatory agents may also be provided

DETAILED DESCRIPTION OF THE INVENTION

The irrigants of the invention have a viscosity and deliquescence adapted to substantially optimize the efficiency of a vibratory scaling and lavage apparatus. The irrigants have ingredients that substantially optimize destruction and removal of infectious bacteria from the sulcus and other areas of the mouth.

The irrigants do not contain substances that inhibit the flow of fluid through the scaling and/or lavage apparatus. The irrigants are also characterized in that they contain hydrogenated starch hydrolysate to replace polyhydric polyols as sweetener/flavor enhancing compounds, especially glycerin and sorbitol The compositions are palatable and effective and yet are relatively non-sticky when allowed to dry on the hands. Hydrogenated starch hydrolysate compounds are oligomers of sorbitol whose apparent sweetness covers a broad range from sweeter than, to much less sweet than sorbitol. Similarly the higher oligomers have lesser humectancy decreasing with molecular weight, and are similarly less deliquescent, so that upon drying the residue of irrigants of the invention may be formulated to avoid residual stickiness and clogging tendency in the scaling/lavage apparatus. Also, additives are selected to inhibit foaming of the fluids so that the view of the field of treatment is not obstructed.

Irrigants comprise a medicament and a vehicle.

As used herein, the term medicament includes antibacterial solutions adapted to fight bacteria associated with periodontal disease or dental caries, solutions adapted to increase resistance to dental caries such as fluoride solutions, surfactants adapted to chemically clean the sulcus and teeth of calculus, plaque and endotoxins as well as solutions containing chemicals used to promote healing Medicaments comprise surfactants or chemicals with surfactant properties. These may include water soluble or dispersible aliphatic or substituted aliphatic sulfate salts, especially the sodium, potassium or ammonium salts wherein the organic group is from 8-carbon atoms. Especially preferred is sodium lauryl sulfate. Other detergent or surfactant species may be selected, for example, the polysorbates, Nonoxyls (GAF Corp.), Tweens, Brij and Span brand surfactants, Triton 100, and others known in the art.

Medicaments also comprise calcium chelating compounds to assist in debriding calculus and removing endotoxin from the tooth, and aiding the suspension of particles not dissolved completely. Such chelating agents include citric acid, ethylene diamine tetraacetic acid, ascorbic acid and other compounds known in the art.

Medicaments also comprise astringents such as zinc chloride, strontium fluoride, stannous fluoride, alum and similar salts including those that may provide hemostasis at the operative site Similarly, medicaments also, comprise antimicrobial substances such as phenolic compounds, eugenol, menthol, thymol, eucalyptol, cresol, quaternary compounds including cetyl pyridinium chloride, didecyl dimethyl ammonium chloride, benzothonium chloride, bisdequalinium acetate, trichloro-2-hydroxydiphenyl ether, chlorhexedine, histidine, metranidazole, bacitracin, tetracyclines, polymixin B, etc.

As used herein, quaternary compounds refers to non-toxic quaternary ammonium compounds having a total of 4–40, preferably 4–30 and more preferably 4–24 carbon atoms. Most preferred are quaternary ammonium compounds having 2 alkyl groups of 1–3 carbon atoms, and 2 alkyl groups of 6-14 carbon atoms.

Medicaments further comprise anti-inflammatory compounds such as steroids including hydrocortisone, but especially the non-steroidal anti-inflammatories comprising salicylic acid and its esters and salts, substituted salicylic acid, its esters and salts, salicaldehyde, ibuprofen, fluorprofen, cyclosporins, etc.

As used herein, the term "substituted" is intended to include non-toxic substituents well known in the pharmaceutical art and may include lower alkyl of 1–12, preferably 1–6 carbons; halogen such as fluoride, chloride or bromide; trifluoromethyl; amino and lower alkyl substituted amino; organic acids and esters thereof having from 2–8 carbon atoms; lower alkyl amides; and others that can be easily identified with reference to the prior art.

Other medicaments comprise compounds capable of reacting in situ with antigenic or other biologic factors These may include trypsin inhibitors, prostaglandin inhibitors, and monoclonal or polyclonal antibodies and peptides reactive to such factors Essentially the medicament portion of the irrigant comprises compounds which when properly formulated as an irrigant, are capable of dissolving, suspending, or emulsifying bacteria and bacterial plaque components including calculus, endotoxin, and other antigenic factors when used in conjunction with the ultrasonic scaling device provided, thus permitting them to be flushed from the pocket by the continuous flow of irrigant delivered simultaneously to the site.

The vehicle portion of the irrigant consists essentially of water and may additionally comprise alcohol and/or polyols such as ethanol, glycerin, sorbitol, propylene glycol or other commiscible organic liquids (solvents) to dissolve otherwise immiscible flavors or medicaments within the irrigant, viscosity controlling substances, flavors and sweeteners to overcome otherwise objectionable taste, dyes, and the like. Ingredients are chosen to insure, the stability of the medicament and its efficacy Polyols used in the composition may also comprise polymers or copolymers thereof including interpolymers thereof with ethylene glycol and mixtures thereof. Also, the esters of each of the above listed polyols may be employed in the composition.

As used herein, the term "ester" represents a moiety of a non-toxic organic acid having 1–8, preferably 1–12 and more preferably 1–6 carbon atoms.

The flavoring may comprise any of the natural and synthetic flavor oils and concentrates that are available for the purpose, for example peppermint, spearmint, licorice, coffee, lemon, cherry, rasberry, strawberry, lime, and the like at the discretion and option of the formulator.

The sweeteners include the simple sugars sucrose, glucose, etc. and especially the noncariogenic sweeteners saccharin, xylitol, aspartame, and the like at the option of the formulator.

The flavor enhancers comprise the oligomers of sorbitol, especially the dimers, trimers and tetramers and their mixtures.

Viscosity control materials may include hydrogenated starch hydrolysates, a preferred example of which is Hystar 5875; sorbitol; glycerin; propanediol, and their copolymers and interpolymers, as for example the Polyoxamers.

An especially useful viscosity control agent is hydrogenated starch hydrolysate which may serve as replacement for polyhydric polyols as sweetener/flavor enhancing compounds and replacements for those commonly used, especially glycerin and sorbitol The compounds produced are equally palatable and effective and yet are not sticky when allowed to dry on the hands. Hydrogenated starch hydrolysate compounds are oligomers of sorbitol whose apparent sweetness covers a broad range from sweeter than to much less sweet than sorbitol. Similarly the higher oligomers have lesser humectancy decreasing with molecular weight, and are similarly less deliquescent, so that upon drying the residue of irrigants of the invention may be formulated to avoid residual stickiness and clogging tendency in the scaling/lavage apparatus.

Commercial products based on these are sold under the trade name Hystar, by Lonza Incorporated These are added in a ratio and concentration in which the desirable viscosity, sweetness and flavor persistence are combined with the properties of nonstickiness and nonclogging of the instrumentation. Ethanol is an optional ingredient whose presence is based on the mutual solubility of the various hydrophilic and hydrophobic components, and as a means to control foaming of the composition in use.

Ingredients may serve multiple purposes, for example, the hydrogenated starch hydrolysate component is both a flavor enhancer and viscosity control agent.

The hydrogenated starch hydrolysate component is added at a concentration of 0.5-30%, preferably 1-20% and most preferably 1-15%. The concentration of ethanol is 0-30%, preferably 0-25%, and most preferably 0-20%. The concentration of surfactant is from 0.01-10%, preferably 0.1-5% and most preferably 0.1-3%.

The concentration of the medicament may vary widely depending on its activity but is of the range of 0.001-10%, most preferably 0.001-8%, and most preferably 0.001-5%. Concentrations of water are typically 50-99.5%, preferably 60-99.5%, and most preferably in the range of 70-99 5%.

All percentages are by weight.

Accordingly, the preferred irrigants of the invention comprise water, medicament, surfactant, alcohol, and optionally flavor, sweeteners and dye.

It has been found that antifoaming agents are desirable to ensure uninterrupted flow of irrigant from the apparatus during treatment and to reduce the amount of foaming that takes place in the patient's mouth.

The term treatment is intended to represent any application of the medicament of the invention, including removal of plaque and calculus, and their application to help prevent the occurrence of any of the conditions described herein.

The method of the invention for proplylaxis and/or treatment of teeth and its connecting tissue comprises simultaneously scaling teeth, preferably with a high speed vibrating scaling apparatus, and coutinuously delivering in situ an anti-microbial solution to enhance removal of bacteria and reduce the viable counts of bacteria The method, in certain embodiments, also comprises the use of surfactants to enhance the removal of plaque, calculus and endotoxins by using the ability of the surfactants to disrupt the cell walls or remove by-products of bacterial species causing such infections. It has been found that delivery of a medicament solution by vibratory motion, using the vibrating motion of the scaling apparatus, enhances the ability of the solution to remove the debris of such infections and to reduce the viable counts of bacteria which cause such infections. It has been found that the apparatus is more effective when using the irrigants of the invention, as compared to using water as an irrigant, and conversely, the medicaments are found to be more effective when applied through the vibrating apparatus, as compared to applying the medicaments in a conventional mouthwash. Thus, one aspect of the method of the invention is the continuous delivery in-situ of a solution capable of dissolving, dispersing and/or emulsifying endotoxin by employing, for example, a surfactant in the irrigant used in the invention.

In general the illustrated irrigants of the invention comprise about 70-92% water, about 5-25% denatured ethyl alcohol, about 1-3% hydrogenated starch hydrolysate, about 0.1-5% polysorbate, and about 0.1-3% medicament, flavoring, and coloring.

Accordingly, an exemplary irrigant formulation that includes an astringent comprises about 80-95% water, about 5-20% denatured alcohol, about 1-10% hydrogenated starch hydrolysate, about 0.1-5% polysorbate 80, about 0.01-0.2% sodium citrate, about 0.1-0.2% $ZnCl_2$, about 0.05% sodium saccharin, and about 0.02-1.0% flavoring and coloring.

Exemplary bactericidal irrigants for treating periodontal disease comprise (1) about 75-90% water, about 5-20% denatured alcohol, about 1-10% hydrogenated starch hydrolysate, about 0.1-5% polysorbate 80, about 0.01-0.1% sodium saccharin, about 0.0001% benzoic acid about 0.01-0.2% cetylpyridinium chloride, and about 0.02-1% flavoring and coloring; and (2) about 70-95% water, about 5-25% denatured alcohol, about 1-10% hydrogenated starch hydrolysate, about 0.5-5% polysorbate 80, about 0.01-0.2% chlorhexedine, and about 0.1-2% flavoring and coloring.

Specific compositions of the invention are illustrated by the following examples.

EXAMPLE 1

| | Example 1 | | |
|---|---|---|---|
| | PERCENT: | | |
| INGREDIENTS: | #1 | 1A | 1B |
| Water Purified | 85.3 | 85.5 | 97.1 |
| Hystar 5875 (flavor enhancer) | 2.0 | 2.0 | 2.0 |
| Sodium Saccharin (sweetener) | 0.05 | 0.05 | 0.05 |
| Sodium Citrate (chelating agent) | 0.1 | 0.1 | 0.1 |
| Zinc Chloride (astringent) | 0.15 | — | — |
| FD & C Green #3 (color) | 0.00005 | 0.00005 | 0.0005 |
| FD & C Yellow #10 (color) | 0.00005 | 0.00005 | 0.0005 |
| Tween 80 (surfactant) | 0.5 | 0.5 | 0.5 |
| Flavor | 0.25 | 0.25 | 0.25 |
| SDA-37B, ethanol | 11.6 | 11.6 | 11.6 |

Directions:

-continued

Example 1

Phase A
Add one at a time with stirring to water.
Phase B
Mix Tween and Flavor well. Add alcohol with stirring until clear. Add to A.
pH 5.9 (#1)

EXAMPLE 2

Example 2

| INGREDIENTS: | PERCENT: |
|---|---|
| Water Purified | 83.1 |
| Hystar 5875 (flavor enhancer) | 5.0 |
| Spectradyne G (20% chlorohexidine solution) (medicament) | 0.6 |
| Sodium Saccharin (sweetner) | 0.05 |
| D & C Yellow #10 (color) | 0.000125 |
| D & C Yellow #6 (color) | 0.00025 |
| Tween 80 (surfactant) | 0.5 |
| Flavor | 0.05 |
| SDA-38B, ethanol | 10.0 |
| | 100.0 |

Directions:
Phase A
Add one at a time with stirring to water.
Phase B
Mix Tween and flavor well. Add Alcohol with stirring until clear. Add to A.
pH 5.2

EXAMPLE 3

Example 3

| INGREDIENTS: | PERCENT: | |
|---|---|---|
| | 3 | 3A |
| Water Purified | 87.4 | 87.4 |
| Hystar 5875 (flavor enhancer) | 2.0 | 2.0 |
| Sodium Saccharin (sweetner) | 0.05 | 0.05 |
| Benzoic Acid | 0.0001 | 0.0001 |
| Cetylpyridinium Chloride (medicament) | 0.045 | — |
| FD & C Blue #1 (color) | 0.000025 | 0.000025 |
| D & C Yellow #10 (color) | 0.00025 | 0.00025 |
| Tween 80 (surfactant) | 0.5 | 0.5 |
| Flavor 0.50000 | 0.05 | 0.05 |
| SDA-38B, ethanol | 10.0 | 10.0 |
| | | 100.0 |

Directions:
Phase A
Add one at a time with stirring to water.
Phase B
Mix Tween and Flavor well. Add Alcohol with stirring until clear. Add to A.
pH 5.6 (#3)

until clear. Add to A. pH 5.6 (#3)

EXAMPLE 4

A scaling/lavage apparatus was used to treat eight patients having symptoms of periodontal disease. One side of each patient's mouth was subjected to treatment by the apparatus using water as the irrigant, and the other side of the patient's mouth was treated using the medicants of the invention as irrigant.

The following are the results of the number of aerobic and anaerobic microorganisms recovered from the side treated with medicament as compared to the side where water was used as an irrigant. Results are reported for each individual, since each individual serves as a test and control.

In tests of the effectiveness of the various compositions described herein, the following results were obtained. Bacteria counts were obtained before and after treatment to establish the percentages given below.

| | | % more bacteria killed as compared to water as control | |
|---|---|---|---|
| | | Aerobes % | Anaerobes % |
| Solution of Example 1 | | | |
| Patient 1 | | 89.2 | 67.0 |
| 2 | | 95.3 | 74.8 |
| 3 | | 97.2 | 95.6 |
| 5 | | 94.5 | 85.9 |
| | mean | 94.1 | 80.8 |
| Solution of Example 3 | | | |
| Patient 4 | | 99.4 | 93.8 |
| 6 | | 99.4 | 83.0 |
| 7 | | 98.6 | 98.0 |
| 8 | | 87.5 | 96.0 |
| | mean | 96.3 | 92.7 |

EXAMPLE 5

A laboratory method provided for an inoculum of Streptococcus mutans to be placed within a simulated tooth pocket in a simulated oral cavity. The tip (probe) of the ultrasonic instrument was placed in the pocket and the instrument was run for 30 seconds at full power with a flow rate of 8 ml/min of irrigant. The viable cells recovered from the surface of the simulated oral cavity when water and test irrigants were used was compared The difference between water and test solutions were reported as % microorganisms killed. The prodedure evaluated the affect of the irrigant on airborne bacterial transported from the pocket and recovered from the simulated oral cavity.

| Solution | Description | % Kill |
|---|---|---|
| Example 1 | Active | 95.0 |
| 1A | Placebo | 36.1 |
| 1B | Placebo | 30.3 |
| Example 2 | Active | 99.6 |
| Example 3 | Active | 99.9 |
| 3A | Placebo | 0 |

While present embodiments of the invention and methods of practicing the same have been illustrated and described, it will be recognized by those skilled in the art that this invention may be otherwise variously embodied and practiced within the scope of the following claims.

What is claimed is:
1. A dental irrigant comprising:
(a) about 70 to about 92 percent, by weight of the irrigant, of water;
(b) about 5 to about 25 percent, by weight of the irrigant, of ethyl alcohol;
(c) about 0.5 to about 30 percent, by weight of the irrigant, of hydrogenated starch hydrolysate; and
(d) about 0.01 to about 10 percent, by weight of the irrigant, of surfactant;
said irrigant having the characteristics of being a free flowing liquid substantially free of polyols having substantial humectant tendencies, substantially non-foaming and relatively non-sticky.

2. The dental irrigant of claim 1 wherein said hydrogenated starch hydrolysate is present in an amount of about 1 to about 10 percent, by weight of the irrigant.

3. The dental irrigant of claim 1 wherein said surfactant comprising polysorbate 80.

4. The dental irrigant of claim 1 comprising about 0.02 to about 1 percent, by weight of the irrigant, flavoring and coloring.

5. The dental irrigant of claim 1 comprising medicament chosen from the group chlorhexidine, zinc chloride, stannous fluoride and cetylpyridinium chloride and mixtures thereof including mixtures with other medicaments.

6. The dental irrigant of claim 1 comprising sweeteners.

7. The dental irrigant of claim 1 wherein said hydrogenated starch hydrolysate is present in an amount of about 1 to about 10 percent, by weight of the irrigant; said surfactant comprising polysorbate 80; and said dental irrigant further comprising about 0.02 to about 1 percent, by weight of the irrigant, flavoring and coloring; and a medicament chosen from the group chlorhexidine, zinc chloride, stannous fluoride and cetylpyridinium chloride and mixtures thereof including mixtures with other medicaments.

8. A method for treatment periodontal disease comprising
  (a) simultaneous high speed vibratory scaling and continuous delivering in-situ an irrigant through an ultrasonic dental scaling and lavage apparatus to enhance removal of bacteria and reduce viable counts of bacteria in the mouth, said irrigant comprising:
    (a) about 70 to about 92 percent, by weight of the irrigant, of water;
    (b) about 5 to about 25 percent, by weight of the irrigant, of ethyl alcohol;
    (c) about 0.5 to about 30 percent, by weight of the irrigant, of hydrogenated starch hydrolysate; and
    (d) about 0.01 to about 10 percent, by weight of the irrigant, of surfactant;
  said irrigant having the characteristics of being a free flowing liquid substantially free of polyols having substantial humectant tendencies, substantially non-foaming and relatively non-sticky.

9. The method of treating periodontal disease of claim 8 wherein said hydrogenated starch hydrolysate is present in an amount of about 1 to about 10 percent, by weight of the irrigant.

10. The method of treating periodontal disease of claim 8 wherein said surfactant comprising polysorbate 80.

11. The method of treating periodontal disease of claim 8 wherein said irrigant comprising about 0.02 to about 1 percent, by weight of the irrigant, flavoring and coloring.

12. The method of treating periodontal disease of claim 8 wherein said irrigant comprising medicament chosen from the group chlorhexidine, zinc chloride, stannous flouride and cetylpyrinium chloride and mixture and thereof including mixtures with other medicaments.

13. The method of treating periodontal disease of claim 8 wherein said irrigant comprising sweeteners.

14. The method of treating periodontal disease of claim 8 wherein said hydrogenated starch hydrolysate is present in an amount of about 1 to about 10 percent, by weight of the irrigant; said surfactant comprising polysorbate 80; and said irrigant further comprising about 0.02 to about 1 percent, by weight of the irrigant, flavoring and coloring; and a medicament chosen from the group chlorhexidine, zinc chloride, stannous fluoride and cetylpyridinium chloride and mixtures thereof including mixtures with other medicaments.

* * * * *